United States Patent
Jo et al.

(10) Patent No.: US 9,737,539 B2
(45) Date of Patent: Aug. 22, 2017

(54) SALT OF FUSED HETEROCYCLIC DERIVATIVE AND CRYSTAL THEREOF

(71) Applicant: KISSEI PHARMACEUTICAL CO., LTD., Matsumoto, Nagano (JP)

(72) Inventors: Kazumichi Jo, Joetsu (JP); Hideki Takeuchi, Joetsu (JP)

(73) Assignee: KISSEI PHARMACEUTICALS CO., LTD., Matsumoto, Nagano (JP)

( * ) Notice: Subject to any disclaimer, the term of this patent is extended or adjusted under 35 U.S.C. 154(b) by 0 days.

(21) Appl. No.: 14/867,501

(22) Filed: Sep. 28, 2015

(65) Prior Publication Data

US 2016/0082010 A1    Mar. 24, 2016

Related U.S. Application Data (62) Division of application No. 13/577,832, filed as application No. PCT/JP2011/052719 on Feb. 9, 2011, now Pat. No. 9,169,266.

(30) Foreign Application Priority Data

Feb. 10, 2010 (JP) ................. 2010-027806

(51) Int. Cl.
| | | |
|---|---|---|
| A61K 31/519 | (2006.01) | |
| A61P 35/04 | (2006.01) | |
| A61P 15/10 | (2006.01) | |
| A61P 15/02 | (2006.01) | |
| A61P 13/08 | (2006.01) | |
| A61P 15/08 | (2006.01) | |
| C07D 495/04 | (2006.01) | |
| A61K 9/00 | (2006.01) | |
| A61K 31/14 | (2006.01) | |

(52) U.S. Cl.
CPC .......... *A61K 31/519* (2013.01); *A61K 9/0053* (2013.01); *A61K 31/14* (2013.01); *C07D 495/04* (2013.01)

(58) Field of Classification Search
CPC .......................... C07D 495/04; A61K 31/519
USPC ....................................... 544/278; 514/260.1
See application file for complete search history.

(56) References Cited

U.S. PATENT DOCUMENTS

| | | | |
|---|---|---|---|
| 4,663,348 A | 5/1987 | Chafetz et al. | |
| 2009/0221590 A1 | 9/2009 | Matthews | |
| 2009/0325900 A1 | 12/2009 | Ohno et al. | |

FOREIGN PATENT DOCUMENTS

| | | |
|---|---|---|
| JP | 56-108787 A | 8/1981 |
| JP | 62-5975 A | 1/1987 |
| WO | 90/02748 A1 | 3/1990 |
| WO | 2007/046392 A1 | 4/2007 |
| WO | 2007/096588 A1 | 8/2007 |

OTHER PUBLICATIONS

Berge, Stephen M.et al, "Pharmaceutical Salts", Journal of Pharmaceutical Science, (1977), 66(1), pp. 1-19.
Stahl, P. Heinrich, "Preparation of Water-Soluble Compounds Through Salt Formation", The practice of medicinal chemistry, 2nd Edition, part VI 35, p. 601-614 (2003).
Morissette, Sherry L., "High-throughput crystallization: polymorphs, salts, co-crystals and solvates of pharmaceutical solids" Advanced Drug Delivery Reviews 56 (2004) pp. 275-300.

*Primary Examiner* — Susanna Moore
(74) *Attorney, Agent, or Firm* — Sughrue Mion, PLLC (57) ABSTRACT

The present invention provides 3-[2-fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid choline salt having excellent solubility and storage stability.

9 Claims, 5 Drawing Sheets

SALT OF FUSED HETEROCYCLIC DERIVATIVE AND CRYSTAL THEREOF

CROSS REFERENCE TO RELATED APPLICATIONS

This is a divisional of U.S. patent application Ser. No. 13/577,832 filed on Aug. 8, 2012, which is a National Stage of International Application No. PCT/JP2011/052719 filed Feb. 9, 2011, claiming priority based on Japanese Patent Application No. 2010-027806 filed Feb. 10, 2010, the contents of all of which are incorporated herein by reference in their entirety.

TECHNICAL FIELD

The present invention relates to a compound (chemical name: 3-[2-fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid choline salt; hereinafter, referred to as "compound (A)") represented by the formula:

[Chem. 1]

(A)

that has an antagonistic activity against gonadotropin releasing hormone, and is useful as a preventative or therapeutic agent for a sex hormone-dependent disease such as benign prostatic hypertrophy, hysteromyoma, endometriosis, metrofibroma, precocious puberty, amenorrhea, premenstrual syndrome, dysmenorrheal or the like.

BACKGROUND ART

A compound (hereinafter, referred to as "compound (B)") represented by the formula:

[Chem. 2]

(B)

that has an antagonistic activity against gonadotropin releasing hormone, and is useful as a preventative or therapeutic agent for a sex hormone-dependent disease such as benign prostatic hypertrophy, hysteromyoma, endometriosis, metrofibroma, precocious puberty, amenorrhea, premenstrual syndrome, dysmenorrheal or the like is disclosed in Patent reference 1. The publication merely contains general descriptions of salts as pharmacologically acceptable salts, and does not report specific salts of compound (B).

Patent reference 1: International Publication pamphlet 2007/046392

DISCLOSURE OF THE INVENTION

Problems to be Solved by the Invention

It has been confirmed by the diligent studies conducted by the present inventors that compound (B) described in Patent reference 1 is amorphous or crystalline. One aspect of amorphous is that it is difficult to, for example, isolate and purify in certain quality in the industrial scale, and accordingly crystals are more preferred as drug materials. However, as will be described in the test example below (saturation solubility test), the crystals of compound (B) have a solubility problem. The poor solubility often causes problems in drug absorbability, and may require ingenuity in formulation with compound (B) used as a drug. Use of compound (B) as drug material thus requires improvements in solubility.

Means for Solving the Problems

The present inventors conducted intensive studies over the foregoing problems, and found that 3-[2-fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid.choline salt has considerably high solubility and desirable storage stability, and thus represents a preferred compound as drug material. The present invention has been completed based on these findings.

That is, the present invention relates to:

(1) a compound represented by the above formula (A);

(2) the compound as described in the above (1), which is crystalline;

(3) the compound as described in the above (2), which has characteristic peaks at diffraction angles ($2\theta(°)$) of 7.1, 11.5, 19.4, 20.3, 21.5, 22.0, 22.6, 23.5 and 26.2 in a powder X-ray diffraction diagram;

(4) the compound as described in the above (2), which has characteristic peaks at chemical shift values ($\delta(ppm)$) of 155.8, 149.8, 145.3, 118.0, 113.7, 111.6, 110.3, 98.1, 69.8, 58.7, 57.1 and 55.5 in a $^{13}C$ solid-state NMR spectrum chart;

(5) the compound as described in the above (2), which has characteristic peaks at chemical shift values ($\delta(ppm)$) of −131.6, −145.2 and −151.8 in a $^{19}F$ solid-state NMR spectrum chart;

(6) the compound as described in any one of the above (2) to (5), which has an endothermic peak at around 213° C. in a differential thermal analysis chart;

(7) a pharmaceutical composition which comprises as an active ingredient a compound as described in any one of the above (1) to (6);

(8) the pharmaceutical composition as described in the above (7), which is a gonadotropin releasing hormone antagonist;

(9) the pharmaceutical composition as described in the above (7), which is an agent for the prevention or treatment of a sex hormone-dependent disease, a reproduction regulator, a contraceptive, an ovulation inducing agent or an agent for the prevention of post-operative recurrence of sex hormone-dependent cancers;

(10) a use of a compound as described in any one of the above (1) to (6) for the manufacture of an agent for the prevention or treatment of a sex hormone-dependent disease, a reproduction regulator, a contraceptive, an ovulation inducing agent or an agent for the prevention of post-operative recurrence of sex hormone-dependent cancers;

(11) a method for preventing or treating a sex hormone-dependent disease, a reproductive regulating method, a contraceptive method, an ovulation-inducing method, or a method for prevention of post-operative recurrence of sex hormone-dependent cancers, comprising administering an effective amount of a compound as described in any one of the above (1) to (6); or the like.

Effect of the Invention

Compound (A) of the present invention has excellent solubility and oral absorbability. Further, compound (A) has excellent crystallinity, and excellent storage stability and fluidity. Compound (A) is thus easy to handle, for example, in formulation.

Best Mode for Carrying Out the Invention

Compound (A) of the present invention can be prepared, for example, using the following method. Specifically, for example, a free compound (B), which can be produced by using the method described in Patent reference 1 or by using methods according to this method, is mixed with an equal amount (1.0 equivalent) or a small excess amount of choline hydroxide in a suitable solvent. The mixture is then dissolved under heat, and the solvent is concentrated or added as appropriate, as required. Compound (A) precipitated upon cooling can then be isolated. Further, compound (A) may be purified by recrystallization using the same or similar solvent.

The solvent may be any solvent, provided that it does not interfere with salt formation. Examples of usable solvents include organic solvents, including alcohols such as methanol, ethanol, 1-propanol, 2-propanol, 1-butanol and 2-butanol, ethers such as tetrahydrofuran and diisopropyl ether, and water. A mixed solvent of these also may be used.

Compound (A) of the present invention is extremely useful as an agent for the prevention or treatment of sex hormone-dependent diseases such as benign prostatic hypertrophy, hysteromyoma, endometriosis, metrofibroma, precocious puberty, amenorrhea, premenstrual syndrome, dysmenorrhea, polycystic ovary syndrome, lupus erythematosis, hirsutism, short stature, sleep disorders, acne, baldness, Alzheimer's disease, infertility, irritable bowel syndrome, prostate cancer, uterine cancer, ovary cancer, breast cancer and pituitary tumor, a reproduction regulator, a contraceptive, an ovulation inducing agent, an agent for the prevention of post-operative recurrence of sex hormone-dependent cancers or the like.

Compound (A) according to the present invention may be appropriately mixed with a pharmaceutical carrier used conventionally to prepare a pharmaceutical composition.

The pharmaceutical carrier may be appropriately in combination according to a dosage form as described below. As the pharmaceutical carrier, for example, excipients such as lactose or the like; lubricants such as magnesium stearate or the like; disintegrators such as carboxymethylcellulose or the like; binders such as hydroxypropylmethylcellulose or the like; surfactants such as Macrogol or the like; foamings such as sodium hydrogene carbonate or the like; dissolving aids such as cyclodextrin or the like; acidities such as citric acid or the like; stabilizers such as sodium edentate or the like; pH adjusters such as phosphoric acid salt or the like can be illustrated.

Examples of the dosage form of the pharmaceutical composition according to the present invention include orally-administered agents such as powders, granules, fine granules, dry syrups, tablets, capsules and the like; and parenterally-administered agents such as injections, poultices, suppositories and the like, and orally-administered agents are preferable.

Preferably, the above formulations are prepared in such a way that compound (A) according to the present invention is administered in 0.1 to 1,000 mg per day for adults in the case of orally-administered agents, and in 0.01 to 100 mg per day for adults for injections.

EXAMPLES

The present invention is further illustrated in more detail by way of the following Examples and Test Examples. However, the present invention is not limited thereto.

Example 1

Compound (A)

3-[2-Fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid (3.07 g) and a 46% choline hydroxide aqueous solution (1.64 g) were suspended in a mixed solution of 1-propanol and water (about 1:1 volume ratio; 30 mL), and the mixture was heated and stirred for 15 min at 60° C. 1-Propanol (30 mL) was added to the mixture at 60° C., and the mixture was stirred at room temperature for 1 hour, and for another one hour under ice-cooled conditions. After the precipitate was collected by filtration, and washed twice with 1-propanol (1 mL). The resulting solid was dried under reduced pressure at 40° C. to obtain compound (A) (2.93 g). Further, this compound was heated and stirred at 60° C. in a mixed solvent of 1-propanol and water (about 1:1 volume ratio; 30 mL), and 1-propanol (30 mL) was added to the solution obtained after hot filtration. The mixture was cooled to room temperature, and stirred for 1 hour, and for another one hour under ice-cooled conditions. The precipitated crystals were collected by filtration, and washed twice with a mixed solvent of 1-propanol and water (about 3:1 volume ratio; 1 mL). The resulting crystals were air-dried for 4 days to obtain compound (A) (2.16 g).

$^1$H-NMR (DMSO-$d_6$)($\delta$(ppm)): 3.10 (9H, s), 3.35-3.45 (2H, m), 3.70-3.90 (8H, m), 4.95 (2H, s), 5.47 (1H, brs), 6.44 (1H, s), 6.85-6.95 (1H, m), 7.05 (1H, d, J=11.5 Hz), 7.11 (1H, d, J=7.4 Hz), 7.48 (1H, dd, J=9.7 Hz, 19.5 Hz), 11.14 (1H, brs)

The obtained compound (A) was measured with regard to powder X-ray diffraction, thermal analysis, $^{13}$C solid-state NMR spectrum and $^{19}$F solid-state NMR spectrum under the conditions below to obtain data.

For the powder X-ray diffraction, the crystals were ground with a mortar, and measured with a powder X-ray diffraction apparatus X'Pert Pro MPD (Spectris plc, PANalytical Department) (reflection method; CuKα rays, tube voltage 45 kV, tube current 40 mA).

Figure 1:
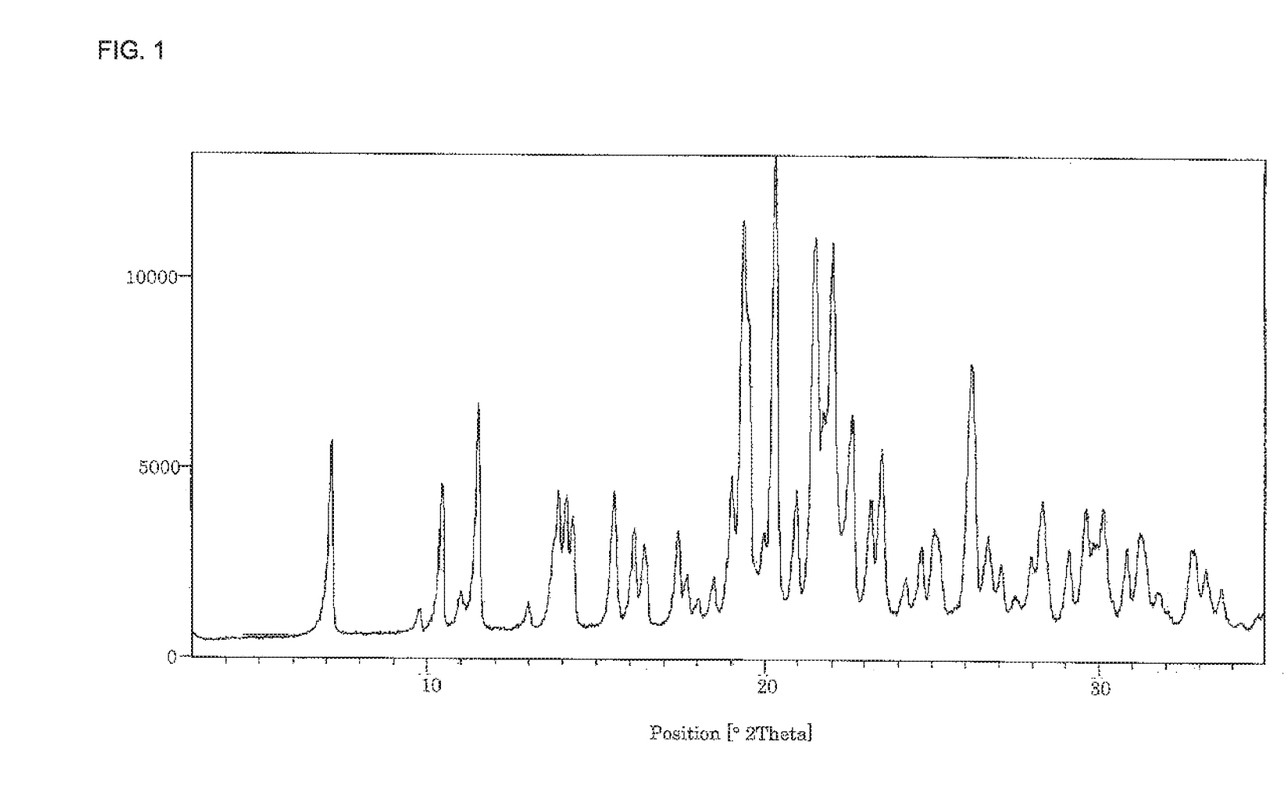
FIG. 1 is a powder X-ray diffraction diagram of compound (A) obtained in Example 1. The vertical axis shows X-ray diffraction intensity (Counts); and the horizontal axis shows diffraction angle (2θ(°)).

The resulting diffraction diagram is shown in FIG. 1, and diffraction angles (2θ(°)) and relative intensities (%) of peaks that had relative intensities of about 20% or higher are shown in Table 1.

TABLE 1

| Diffraction angle (2θ (°)) | Relative intensity (%) |
| --- | --- |
| 7.1 | 38 |
| 10.4 | 32 |
| 11.5 | 48 |
| 13.9 | 31 |
| 14.1 | 29 |
| 14.3 | 24 |
| 15.5 | 31 |
| 16.1 | 23 |
| 16.4 | 20 |
| 17.4 | 22 |
| 19.0 | 34 |
| 19.4 | 86 |
| 20.0 | 22 |
| 20.3 | 100 |
| 21.0 | 31 |
| 21.5 | 83 |
| 22.0 | 82 |
| 22.6 | 46 |
| 23.2 | 29 |
| 23.5 | 39 |
| 25.1 | 22 |
| 26.2 | 57 |
| 26.7 | 22 |
| 28.3 | 29 |
| 29.6 | 27 |
| 30.1 | 27 |
| 31.2 | 22 |

For reasons related to the nature of data in powder X-ray diffraction, the 2θ values and the overall diffraction pattern are important for the recognition of crystal identity. It is common knowledge that the relative intensity in X-ray diffraction patterns fluctuates in a manner that depends on sample conditions and measurement conditions. It should be noted that the 2θ values of diffraction patterns in powder X-ray diffraction may slightly fluctuate depending on sample conditions and measurement conditions.

Figure 2:
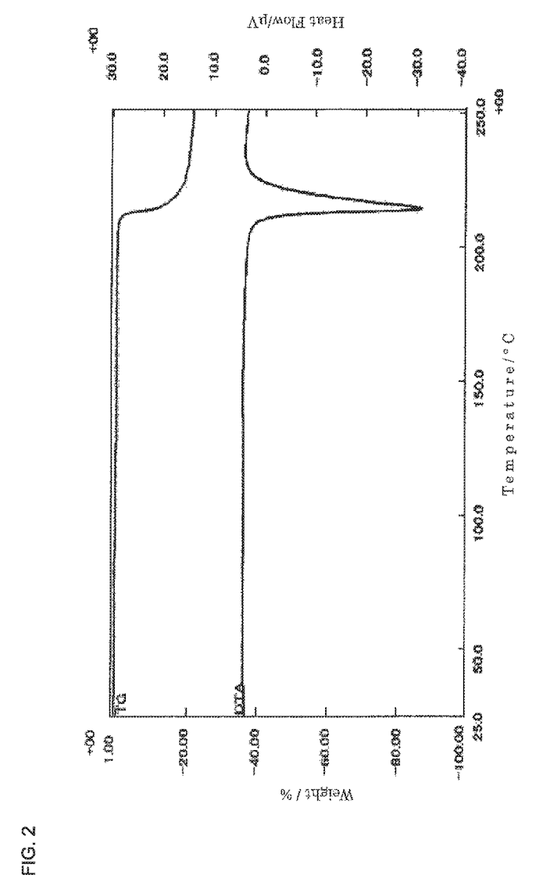
FIG. 2 is a diagram representing the TG-DTA measurement of compound (A) obtained in Example 1. The vertical axis (left) shows weight (%) in a thermogravimetric (TG) curve; the vertical axis (right) shows heat flux (μv) in a differential thermal analysis (DTA) curve; and the horizontal axis shows temperature (° C.).

For the thermal analysis, measurements were made using a thermogravimetric differential thermal analyzer TG-DTA TG8120 (Rigaku Corporation) (Heating rate: 10° C./min; reference material: aluminum oxide). The resulting chart is shown in FIG. 2.

Endothermic peak: around 213° C.

Note that the endothermic peak in thermal analysis may slightly fluctuate depending on sample conditions and measurement conditions.

Figure 3:
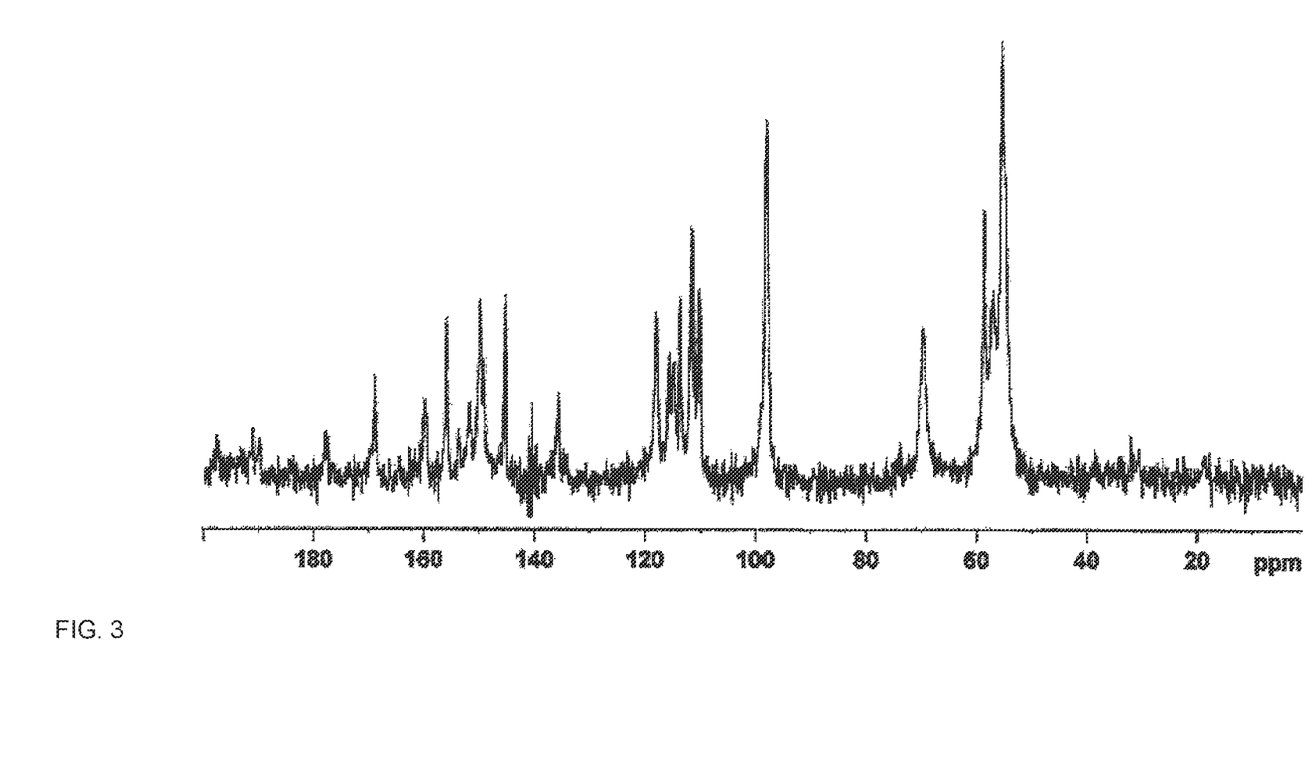
FIG. 3 is a $^{13}$C solid-state NMR spectrum chart of compound (A) obtained in Example 1. The vertical axis shows intensity; and the horizontal axis shows chemical shift value (δ(ppm)).

For the $^{13}C$ solid-state NMR spectral measurement, a sample was charged into a 4-mm zirconia rotor, and measured with a Bruker Avance DRX500 (rotation speed 10 kHz) using the CP/MAS technique. The resulting spectrum chart is shown in FIG. 3.

Note that the chemical shift values in the $^{13}C$ solid-state NMR spectrum may slightly fluctuate depending on sample conditions and measurement conditions.

Figure 5:
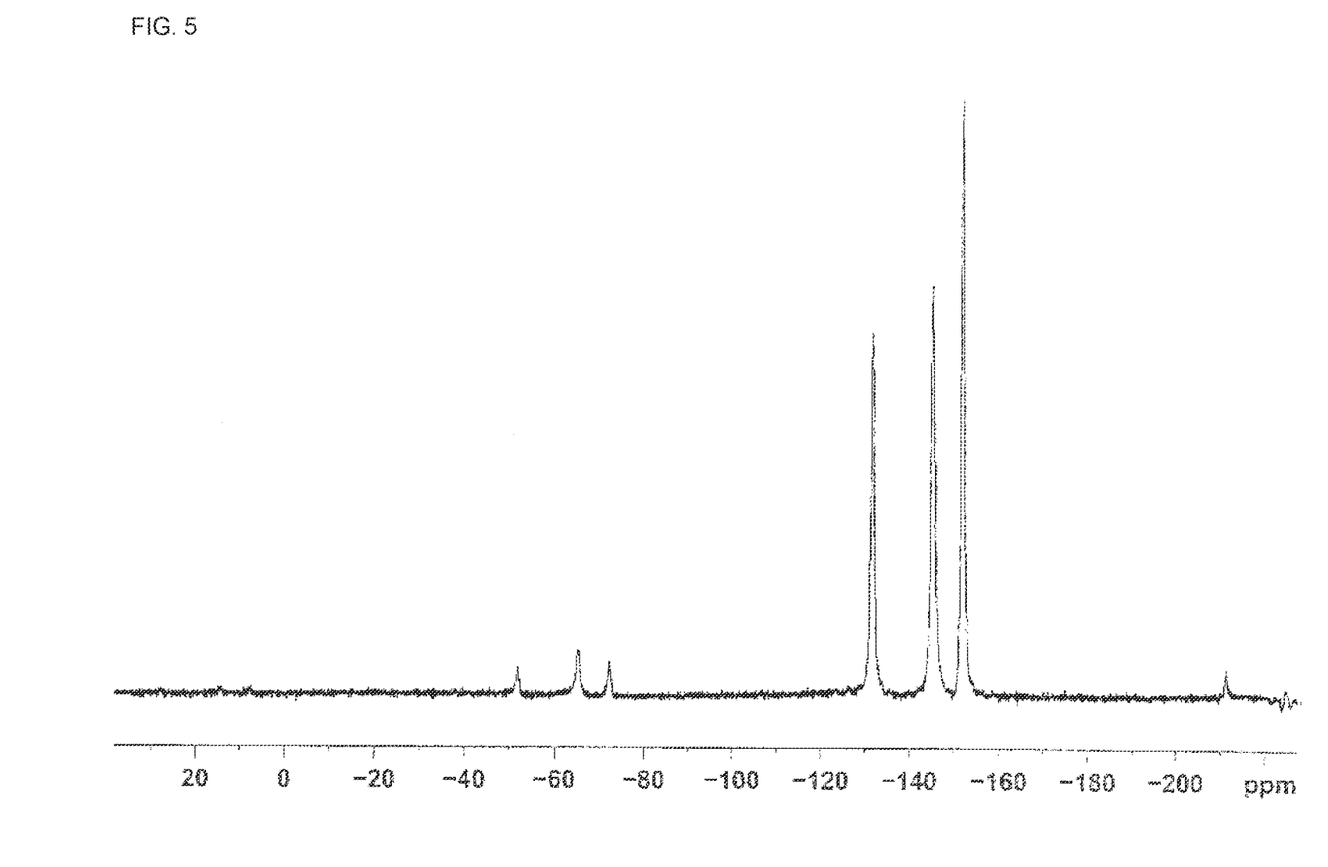
FIG. 5 is a $^{19}$F solid-state NMR spectrum chart of compound (A) obtained in Example 1. The vertical axis shows intensity; and the horizontal axis shows chemical shift value (δ(ppm)).

For the $^{19}F$ solid-state NMR spectrum measurement, a sample was charged into a 2.5-mm zirconia rotor, and measured with a Bruker Avance III 400 WideBore (rotation speed 30 kHz) using the MAS technique. The spectrum was observed with reference to the external standard sample polyvinylidene fluoride (PVDF) set to resonate at −91.2 ppm. The resulting spectrum chart is shown in FIG. 5.

Note that the chemical shift values in the $^{19}F$ solid-state NMR spectrum may slightly fluctuate depending on sample conditions and measurement conditions.

Example 2

Compound (A)

3-[2-Fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid (4.07 g), a 46% choline hydroxide aqueous solution (2.18 g), 2-propanol (200 mL) and water (100 mL) were mixed, and heated for 15 min at 40° C. After removing the insoluble matter by filtration, the resulting solution was concentrated, and 2-propanol (80 mL) and diisopropyl ether (80 mL) were added. The mixture was then stirred at room temperature for about 1 hour, and then for about 4 hours under ice-cooled conditions. The precipitated solid was collected, and dried at 90° C. overnight under reduced pressure (yield 3.59 g). A mixed solution of ethanol and water (about 1:1 volume ratio; 25 mL) was then added to the resulting solid (3.56 g). The mixture was heated to 65° C., and subjected to hot filtration after adding a mixed solution of ethanol and water (1:1 volume ratio; 10 mL) at the same temperature. The resulting solution was stirred while being allowed to cool at room temperature for 2 hours, and further stirred at room temperature for about 1 hour after adding ethanol (20 mL). The mixture was further stirred at room temperature for about 1 hour after adding ethanol (20 mL), and further stirred overnight under ice-cooled conditions. The solid was collected from the mixture, washed with ethanol (5 mL), and dried by blowing nitrogen. The solid was further dried at 40° C. overnight under reduced pressure to obtain compound (A) (2.43 g). The obtained compound (A) was measured for powder X-ray diffraction in the same manner as in Example 1. The result confirmed that the compound (A) had the same crystal form observed in Example 1.

$^{1}H$-NMR (DMSO-$d_6$)(δ(ppm)): 3.10 (9H, s), 3.35-3.45 (2H, m), 3.70-3.90 (8H, m), 4.96 (2H, s), 5.38 (1H, brs), 6.43 (1H, s), 6.85-6.95 (1H, m), 7.05 (1H, d, J=11.5 Hz), 7.10 (1H, d, J=7.4 Hz), 7.47 (1H, dd, J=9.7 Hz, 19.5 Hz), 11.11 (1H, brs)

Comparative Example 1

Crystals of Compound (B)

Figure 4:
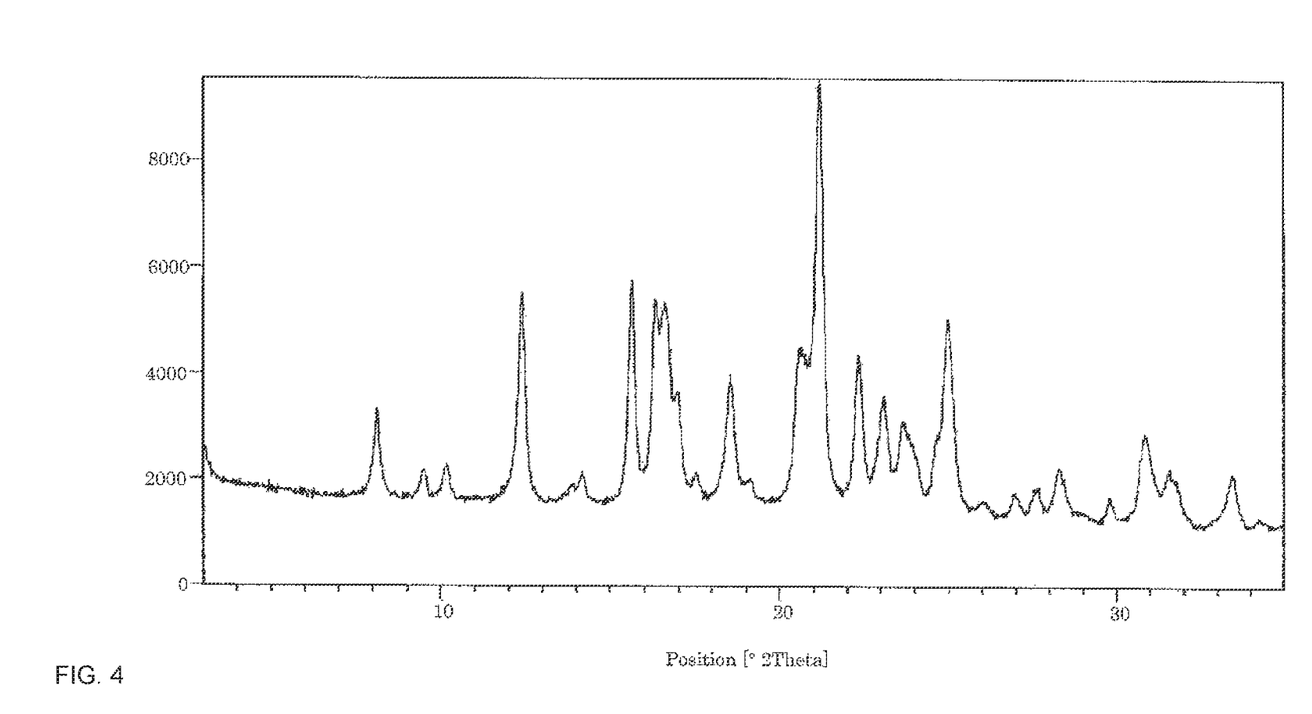
FIG. 4 is a powder X-ray diffraction diagram of compound (B) obtained in Comparative Example 1. The vertical axis shows X-ray diffraction intensity (Counts); and the horizontal axis shows diffraction angle (2θ(°)).

Ethyl acetate (0.1 mL) was added to an amorphous solid of 3-[2-fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid (10 mg), and the suspension was heated to 50° C. The mixture was then dried by blowing nitrogen gas. The resulting solid was further heated to 70° C., and dried overnight under reduced pressure to obtain crystals of compound (B) (10 mg). The obtained crystals of compound (B) were measured for powder X-ray diffraction in the same manner as in Example 1. The resulting diffraction diagram is shown in FIG. 4.

Comparative Example 2

Crystals of Compound (B)

3-[2-Fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid (0.69 g) was suspended in diisopropyl ether (10 mL), and the mixture was stirred at 60°

C. for 3 hours under heat. The mixture was stirred at room temperature overnight, further for 1 hour under ice-cooled conditions. The solid was collected by filtration, and dried under reduced pressure to obtain crystals of compound (B) (0.65 g). The obtained crystals of compound (B) were measured for powder X-ray diffraction in the same manner as in Example 1. The result confirmed that the compound (B) had the same crystal form observed in Comparative Example 1.

Comparative Example 3

3-[2-Fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid.1/2N,N'-dibenzylethylenediamine Salt (Hereinafter, Referred to as "Compound (C)")

Acetonitrile (10 mL), N,N'-dibenzylethylenediamine (94.5 mg), and 3-[2-fluoro-5-(2,3-difluoro-6-methoxybenzyloxy)-4-methoxyphenyl]-2,4-dioxo-1,2,3,4-tetrahydrothieno[3,4-d]pyrimidine-5-carboxylic acid (200 mg) were mixed. The mixture was suspended at about 60° C., and stirred while being allowed to cool at room temperature. The solid was collected from the mixture by filtration, and dried at about 60° C. overnight under reduced pressure (247 mg).

$^1$H-NMR (DMSO-$d_6$)(δ(ppm)): 2.83 (2H, s), 3.79 (3H, s), 3.80 (3H, s), 3.87 (2H, s), 4.95 (2H, s), 6.85-6.95 (1H, m), 6.98 (1H, s), 7.09 (1H, d, J=11.5 Hz), 7.19 (1H, d, J=7.5 Hz), 7.25-7.55 (6H, m)

Test Example 1

Saturation Solubility Test

The compound (A) obtained in Example 2, the compound (B) crystals obtained in Comparative Example 2, and the compound (C) obtained in Comparative Example 3 were suspended in water, or in 1st fluid for dissolution test (hereinafter, referred to as "1st fluid") or 2nd fluid (hereinafter, referred to as "2nd fluid") described in the Reagents.Test Solutions for General Tests, the Japanese Pharmacopoeia, 15th Edition. The suspensions were incubated at 37° C. After filtering a part of the suspensions, the concentrations of the resulting filtrates were measured by HPLC, and the saturation solubilities were calculated and compared. The HPLC measurement conditions are as follows.

Measurement Conditions

Detector: Ultraviolet and visible spectrophotometer/wavelength: 225 nm
Column: GL Science Inertsil ODS-3, 5 μm, 4.6×250 mm
Column temperature: a constant temperature of around 35° C.
Flow rate: 1.0 mL/min
Mobile phase A: 10 mM potassium dihydrogen phosphate aqueous solution adjusted to pH 5.5 with potassium hydroxide aqueous solution
Mobile phase B: Acetonitrile
Mobile phase ratio 0 to 30 min: mobile phase A/mobile phase B=70/30

The saturation solubility values of compound (A), compound (B) crystals, and compound (C) in water, 1st fluid, and 2nd fluid are shown in Table 2. In water, compound (A) had a saturation solubility about 600 times and about 60 times higher than those of compound (B) crystals and compound (C), respectively. The saturation solubility of compound (A) in 1st fluid was about 30 times and about 2 times higher than those of compound (B) crystals and compound (C), respectively. In 2nd fluid, the saturation solubility of compound (A) was about 10 times and about 70 times higher than those of compound (B) crystals and compound (C), respectively. These results thus confirmed significant improvements in the solubility of compound (A) over compound (B) crystals and compound (C).

TABLE 2

| | The compound (A) obtained in Example 2 | The crystals of the compound (B) obtained in Comparative Example 2 | The compound (C) obtained in Comparative Example 3 |
|---|---|---|---|
| Water | 4165 | 7 | 68 |
| 1st fluid | 4 | 0.14 | 2 |
| 2nd fluid | 3738 | 367 | 52 |

Unit: μg/mL

Test Example 2

Assay for Oral Absorbability

1) Preparation of Sample for Drug Concentration Measurement by Administration Through Tail Vein SD rats (Charles River, male, 7 weeks of age, 170 to 210 g) were used as experimental animals after fasting the rats overnight. N,N-dimethylacetamide (0.2 mL), saline (0.798 mL) and 2N—NaOH (0.002 mL) were added in these amounts with respect to 1 mg of the compound (B) to prepare a 1.0 mg/mL solution. The solution was then administered in a 1 mL/kg dose (1 mg/kg) through the tail vein under no anesthesia (3 samples). The intravenous administration through tail was performed using a 26 G injection needle and a 1 mL syringe. Blood was collected through the subclavian veins after 2, 15, 60, 120, 240 and 360 minutes from the intravenous administration through tail. The blood was centrifuged, and the plasma was used as a sample for blood drug concentration measurement.

2) Preparation of Sample for Drug Concentration Measurement by Oral Administration SD rats (Charles River, male, 7 weeks of age, 220 to 290 g) were used as experimental animals after fasting the rats overnight. A 0.5% methylcellulose aqueous solution (5 mL) was added with respect to 3 mg of compound (A) or compound (B) (in terms of a free compound) to prepare a 0.6 mg/mL drug solution. Each solution was orally administered to the rats in a 5 mL/kg dose (3 mg/kg) (3 samples each). The oral administration was performed using a rat sonde and a 2.5-mL syringe. Blood was collected through the subclavian veins under no anesthesia after 15, 30, 60, 120, 240, 360 and 480 minutes from the oral administration. The blood was centrifuged, and the blood plasma was used as a sample for blood drug concentration measurement.

3) Drug Concentration Measurement

A suitable internal standard substance solution (0.1 mL) was added to the blood plasma (0.025 mL) obtained in 1) and 2) using an ordinary method. Then, acetonitrile (0.875 mL) was added to remove the protein. After centrifugation, the supernatant (0.005 mL) was injected to LC-MS/MS. Blood plasma drug concentration was measured using the LC-MS/MS technique under the conditions below. Note that the standard curve was created by appropriately adding an internal standard substance and a target substance to a blank blood plasma (0.05 mL) using an ordinary method, followed by the foregoing procedures.

LC

Device: Agilent 1100

Column: Capcellpak MGIII 5 μm 4.6×50 mm

Mobile phase A: 10 mM ammonium acetate aqueous solution

Mobile phase B: Acetonitrile (Mobile phase ratios are presented in Table 3)

Column temperature: 40° C.

Flow rate: 0.5 mL/min

MS/MS

Device: API-4000

Ionization method: ESI (Turbo Ion Spray)

TABLE 3

| Time (minutes) | A (%) | B (%) |
|---|---|---|
| 0.0 | 90 | 10 |
| 3.0 | 90 | 10 |
| 4.0 | 10 | 90 |
| 7.0 | 10 | 90 |
| 7.1 | 90 | 10 |
| 12.0 | 90 | 10 |

The bioavailability of the compound (A) was about 59%, and desirable oral absorbability was confirmed. Further, the maximum drug concentration time (Tmax) was 35 min in the compound (A), compared to 200 min in the compound (B), and because the compound (A) was quickly absorbed after the administration, a fast onset of action is expected.

Bioavailability (%) was calculated from the value of the area under the blood drug concentration-time curve determined by using a WinNonlin Professional (Pharsight Corporation) from the blood drug concentration at each time point obtained as above after the intravenous administration of the compound (B) through tail and the oral administration of the compound (A) or the compound (B).

Test Example 3

Stability Test

The compound (A) obtained in Example 2 was stored under 90° C. open conditions to examine stability. In stability measurement, the purity of a sample was measured by HPLC at the initial point and after 8 days, and the results were compared. The HPLC measurement conditions are as follows.

Measurement Conditions

Detector: Ultraviolet and visible spectrophotometer/wavelength: 225 nm

Column: GL Science Inertsil ODS-3, 5 μm, 4.6×250 mm

Column temperature: Constant temperature around 35° C.

Flow rate: 1.0 mL/min

Mobile phase A: 10 mM potassium dihydrogen phosphate aqueous solution adjusted to pH 5.5 with potassium hydroxide aqueous solution Mobile phase B: Acetonitrile (Mobile phase ratios are shown in Table 4)

Area measurement range: 54 minutes from the start of the analysis. Areas of the peaks in the blank were excluded from the calculations.

The measurement results are shown in Table 5.

TABLE 4

| Time (minutes) | A (%) | B (%) |
|---|---|---|
| 0 | 70 | 30 |
| 20 | 70 | 30 |
| 40 | 30 | 70 |
| 60 | 30 | 70 |
| 60.1 | 70 | 30 |
| 80 | 70 | 30 |

TABLE 5

| | The compound (A) obtained in Example 2 | |
|---|---|---|
| Measurement point | Initial point | After 8 days |
| Purity (%) | 99.6 | 99.6 |

As described above, the results of Test Examples 1 to 3 show that the compound (A) of the present invention has excellent solubility, oral absorbability and storage stability, and thus represents an excellent compound capable of solving the problems relating to the physical properties of the free compound (B).

INDUSTRIAL APPLICABILITY

The compound (A) according to the present invention has excellent solubility and other desirable physical properties, and is useful as drug material, and suited for the industrial production of drugs.

The invention claimed is:

1. A method for treating a sex hormone-dependent disease selected from the group consisting of benign prostatic hypertrophy, hysteromyoma, endometriosis, metrofibroma, precocious puberty, amenorrhea, premenstrual syndrome, dysmenorrhea, polycystic ovary syndrome, hirsutism, short stature, infertility, irritable bowel syndrome and prostate cancer, comprising administering an effective amount of a compound represented by the formula:

(A)

2. The method of claim 1, wherein said sex-hormone dependent disease is endometriosis.

3. The method of claim 1, wherein said sex-hormone dependent disease is hysteromyoma.

4. The method of claim 1, wherein said sex-hormone dependent disease is prostate cancer.

5. The method of claim 1, wherein said compound is administered orally.

6. The method of claim 1, wherein said compound is crystalline.

7. The method of claim 1, wherein said compound has characteristic peaks at diffraction angles (2θ(°)) of 7.1, 11.5, 19.4, 20.3, 21.5, 22.0, 22.6, 23.5, and 26.2 in a powder X-ray diffraction diagram.

8. The method of claim 1, wherein said compound has characteristic peaks at chemical shift values (δ(ppm)) of 155.8, 149.8, 145.3, 118.0, 113.7, 111.6, 110.3, 98.1, 69.8, 58.7, 57.1, and 55.5 in a $^{13}$C solid-state NMR spectrum.

9. The method of claim 1, wherein said compound has characteristic peaks at chemical shift values (δ (ppm)) of −131.6, −145.2, and −151.8 in a $^{19}$F solid-state NMR spectrum.

* * * * *